United States Patent [19]

Krempl et al.

[11] Patent Number: 4,577,105

[45] Date of Patent: Mar. 18, 1986

[54] METHOD OF DETERMINING MASSES OF ABSORBING COMPONENTS OF A SAMPLE IN A TEST VOLUME AND A DEVICE FOR IMPLEMENTATION OF THIS METHOD

[75] Inventors: Peter W. Krempl; Wolfgang Schindler, both of Graz, Austria

[73] Assignees: AVL Gesellschaft für Verbrennungskraftmaschinen und Messtechnik; Hans List, both of Graz, Austria

[21] Appl. No.: 602,391

[22] Filed: Apr. 20, 1984

[30] Foreign Application Priority Data

Apr. 21, 1983 [AT] Austria .................................. 1468/83

[51] Int. Cl.[4] ................................................. G01J 1/00
[52] U.S. Cl. ..................................... 250/343; 356/437
[58] Field of Search ................. 250/343, 344; 356/437, 356/438, 439

[56] References Cited

U.S. PATENT DOCUMENTS 3,805,074 4/1974 McCormack ......................... 250/343
3,958,122 5/1976 Jowett et al. ........................ 250/344

FOREIGN PATENT DOCUMENTS 2422174 12/1974 Fed. Rep. of Germany .
2557508 7/1976 Fed. Rep. of Germany .
1470144 4/1977 United Kingdom .

Primary Examiner—Janice A. Howell
Attorney, Agent, or Firm—Watson, Cole, Grindle & Watson

[57] ABSTRACT

A test volume and a reference volume are irradiated by separate beams of an infrared source, and the two beams are subsequently fed to a detector in periodical alternation. The time constant of the detector is small compared to the period of this alternation. From the measured differences in intensity the masses of the absorbing components of a sample in the test volume are determined. During each period the value of the detector signal is sampled by an evaluation unit at least once while either the test beam or the reference beam is being present at the detector. For separate determination of different sample components, radiation of different defined frequency bands is fed to the detector during each period, and the intensity of the test beam is determined at each of the different frequencies whereas that of the reference beam is determined at one of these frequencies at least.

7 Claims, 5 Drawing Figures

METHOD OF DETERMINING MASSES OF ABSORBING COMPONENTS OF A SAMPLE IN A TEST VOLUME AND A DEVICE FOR IMPLEMENTATION OF THIS METHOD

BACKGROUND OF THE INVENTION

This invention relates to a method of determining masses of absorbing components of a sample in a test volume, using electromagnetic radiation in the infrared region of the spectrum passing in separate beams through both the test volume and a reference volume, and both the test beam and the reference beam being fed to a detector, alternating periodically, and the masses to be measured being obtained from the differences in radiation intensity. The time constant of the detector used is smaller by at least one order of magnitude than the period of alternation between test beam and reference beam.

Furthermore, the invention relates also to a device for implementation of this method.

DESCRIPTION OF THE PRIOR ART

Conventional methods of determining the masses of sample components are based on splitting the radiation of an infrared source into two partial beams alternatingly arriving at a common detector. One of these beams traverses a test volume containing the absorbing material whose extinction behaviour is to be measured for the purpose of mass determination, whereas the other one is used as a reference beam. Frequently care is taken that the test beam prior to passage of the the test volume and the reference beam have the same intensity and that the beams travel the same optical paths, although this is not essential for the success of the method.

In some of the known devices for implementing the above method detectors are used whose output signal is directly proportional to the difference in intensity of the two beams, e.g., pyroelectric or "Golay" detectors. The disadvantage of such devices is that both the test beam and the reference beam have to be applied to the detector in such a way as to avoid complete blackout or double exposure of the detector at any time, which requires a considerable amount of adjustment, e.g., of mechanical chopper disks, and, consequently, is rather susceptible to failure.

Moreover, detectors are known which take a relatively long time, i.e., several milliseconds, until their output signal attains a constant value if they are exposed to infrared radiation, thus yielding a signal proportional to the incident radiation after the response time. In this context the thermopiles or thermocouples should be mentioned which are frequently used in infrared spectrometers. In this type of detector blackout periods or double exposures are of little consequence if they are short relative to the period of the measurement proper. Absorptions in the percentage range may be measured with this kind of device, provided that the period of measurement is not too short, i.e., in each partial measurement of the individual beams the constant final value of the detector signal must be achieved. On the other hand, frequencies above 20 Hz cannot be determined by means of such devices, which will affect, above all, evaluation of dynamic changes of the absorbing components of a sample.

In German laid-open print No. 24 22 174 a method and device of the above type have been described, for instance, in which a detector is used whose time constant is smaller by at least one order of magnitude than the period of alternation between test beam and reference beam. Although this will permit measurements with a time resolution of less than 0.25 seconds, the technical complexity and cost involved in building such a device is considerable, especially if several different sample components are to be measured separately, because of the use of several identical test and reference cuvettes, each of them requiring a separate filter passing different frequencies which is permanently attached behind each cuvette in the carrier wheel.

SUMMARY OF THE INVENTION

It is an object of the present invention to avoid the above disadvantages of the known methods and devices, and to describe a method of the aforementioned type as well as a device for its implementation that will not deliver faulty values due to blackouts or double exposure at the detector, and will permit measurement of dynamic processes with a high resolution in time, i.e., 100 Hz and more, in addition to being simple in design and comparatively inexpensive.

According to the present invention this is achieved by sampling the momentary value of the detector signal at least twice during a period, i.e., at least once each for determining the intensity of test beam and reference beam, the sampling time being short compared to the period itself, and by feeding in a given time sequence radiation of at least two defined frequency bands which is derived from one radiation source, to one and the same detector during each period. For the separate determination of at least two sample components, the intensity of the test beam being obtained for each of the defined frequencies and that of the reference beam for at least one of these frequencies during each period.

The use of a fast detector with a small time constant will permit a very short read-in time, which will not only help to avoid the negative effects of exposure errors but will also enable several signal values which may be frequency-selected, e.g., to be obtained and processed within one period of measurement. Suitable detectors which have been developed recently, include units which will change their electrical properties due to quantum effects in the detector material, or will develop electromotive forces. The response times of such detectors to changes in radiation intensity are in the micro-second range.

Basically, the method described by this invention is aimed at examining absorption at defined frequencies in order to permit separate determination of at least two different components of the sample. This is achieved by subsequently feeding radiation of the selected and defined frequencies into the common detector within one period, the signal value of the test beam being read for each frequency, and that of the reference beam for at least one of these defined frequencies. For this purpose a radiation source may be used which will emit the defined frequencies desired one after the other, or frequency-selecting units, e.g., interference filters, may be introduced into the radiation path of a broad-band source. The signal from the detector is read by the evaluation circuit at that point in time at which the full intensity of the particular frequency selected is present at the detector. The value of the detector signal will vary between a minimum at total darkness and a maximum at exposure to the reference beam, with the signal value during exposure to the test beam after passage of the test volume usually being below the above maximum if the test apparatus has been adjusted correctly. The minimum value of the detector signal need not necessarily be recorded in the evaluation unit which could be adjusted such that its maximum output signal would correspond to an intensity loss in the test volume of 0% and its minimum output signal to an intensity loss of 10%, for instance, which would offer a good way of resolving much smaller losses of intensity than would be the case if the minimum output signal were related to an intensity loss of 100%, i.e., complete blackout.

For various spectroscopic applications it will be of advantage, however, if the momentary value of the detector signal is additionally sampled at a point in time at which no radiation arrives at the detector, as is proposed in a further development of the invention. In this variant the amplifier which is usually contained in the evaluation unit, must be adjusted in such a way as to ensure that the minimum value of its output signal will reliably correspond to an intensity loss of 100%.

Although the method proposed here can be used for determining the mass of any substance absorbing infrared radiation, it is of particular importance for the measurement of aerosol particles in the waste gas of incinerator systems or internal combustion engines. So far the amount of aerosol particles has been determined by measuring the extinction of visible light; this method ensures good time resolution and high sensitivity to extinction changes. This extinction cannot be correlated with the mass of aerosol particles, however, since the wavelength of light is of the same order of magnitude as the particle diameters: in the optical Mie-range. In this range extinction and mass can be correlated only if the particle diameter is known precisely. The wavelength of infrared radiation is much greater than the diameters of particles from internal combustion engines, however, and in this optical Raleigh range extinction is proportional to the mass load of particles. Use of the method described by the present invention for the measurement of smoke gas therefore signifies a considerable improvement of the techiques of waste gas measurement.

A further embodiment of the method according to the present invention provides that the mass emission of graphitic aerosol particles in exhaust gas should be measured by means of a narrow frequency band with wavelengths around 3.95 $\mu$m.

With these infrared frequencies absorption may be used as a measure of particle loads of exhaust gas, and, besides, will permit determination of the graphitic component of the aerosol.

A particularly advantageous embodiment of the invention proposes that an absorber of defined absorption be introduced into the radiation path with a period amounting to an integral multiple of the period of alternation between test and reference beam. This will provide a good method of calibrating the measurement values for the present invention. Since the intensity of the radiation source may change in the course of prolonged measurement continual calibration is recommended, e.g., by introducing an absorber of defined absorption into the path of the reference beam, if possible, at every n-th period of the measurement (n being an integer greater than 2 or, preferably, equal to 2). Calibration is also possible, however, if the absorber is introduced into the test beam. Using the difference between the detector signals with and without an absorber in the reference beam, absorption in the test volume can be calculated from the corresponding detector signal. The effective time resolution of the method as a whole is slightly reduced by this continual calibration, which is of no relevance, however.

For a device for implementing the method, comprising a broad-band radiation source which emits at least one test beam passing through a test volume and one reference beam passing through a reference volume in the infrared region of the spectrum, and further comprising a unit for alternately feeding these beams to a common detector connected to an evaluation unit, a preferred embodiment of the invention provides that the above unit for alternately feeding the test and reference beams to the detector contains at least one mechanical gear system with selection elements, preferably, as described, e.g., in British Patent Specification No. 1,470,144 or German laid-open print No. 25,57,508, configured as a rotating disk with openings, and that frequency filters passing radiation of the defined frequency bands be placed in the openings of this selection element. The detector signal is accepted by the evaluation unit only at those points in time at which the test or reference beam is passing through the respective frequency filter at maximum intensity. This results in a simple and robust design of the device in which, due to the rapid response of the fast detector, small maladjustments will not cause errors. Suitable markings, e.g., notches around the circumference of the rotating disk holding the frequency filters, which cooperate with non-contact proximity switches or light-barriers, can be used to define precisely those points in time at which the particular frequency filter is at its optimum position in the radiation path.

According to another embodiment the unit for alternately feeding test and reference beams to the detector contains at least one frequency-selective element in the radiation path between test/reference volume and detector, which can be tuned optoelectronically. The detector signal is accepted by the evaluation unit at those points in time at which the optoelectronic unit is selecting one of the defined frequency bands from the test or reference beam. Use of these optoelectronically tuned frequency filters which have been described before, will guarantee a simple design and reliable performance of the device.

Yet another embodiment of the invention suggests the use of an infrared radiation source which can be periodically tuned to the defined frequency bands, the detector signal again being accepted by the evaluation unit for those points in time only when the radiation source is emitting one of the desired frequencies. In this way the unit in front of the detector for alternately feeding different frequencies to the latter, may be dispensed with altogether since the radiation source will deliver only the desired frequencies in the desired periodical sequence.

According to a preferred embodiment of the invention the detector may be configured as one of the resistors in a bridge circuit in the evaluation unit, another resistor in this circuit being adjusted such that the output voltage between two connector points of the bridge circuit may be adjusted to a defined value, preferably zero, during an adjustment process, this output voltage corresponding either to the minimum or to the maximum exposure of the detector. This will be of special advantage if the detector is configured as a photoresistor since this will contribute towards a simple design of the evaluation unit and easy adjustment of the assembly.

The bridge circuit represents a simple and advantageous method of measuring changes in resistance, especially if there is a change in exposure of the photoresistor. The most sensitive measurement of resistance changes by means of the bridge circuit is achieved by adjusting a second resistor in such a way as to obtain a zero output voltage of the bridge in a reference situation of the experiment, in the present set-up, e.g., at maximum exposure (less favorable, although possible, at complete darkness—zero exposure).

DESCRIPTION OF THE DRAWINGS

Following is a more detailed description of the invention as illustrated by the enclosed drawings, in which.

DESCRIPTION OF THE PREFERRED EMBODIMENTS

Figure 1:
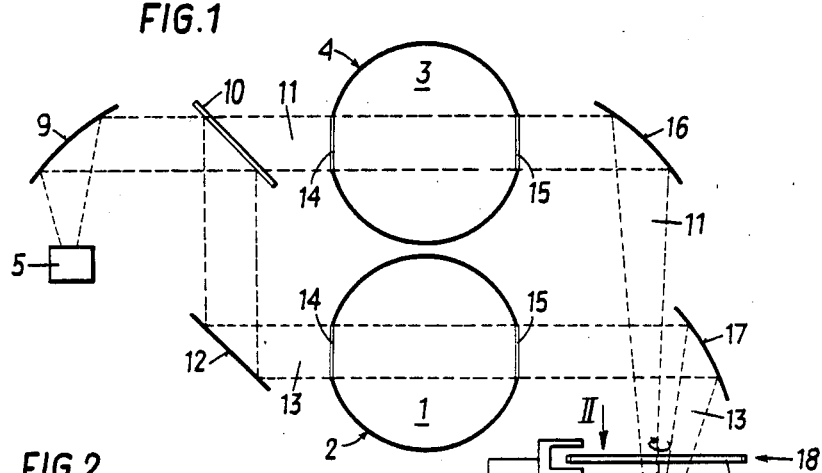
FIG. 1 presents a schematical view of an embodiment according to the invention.

The assembly in FIG. 1 essentially comprises a test chamber 2 containing a test volume 1, a reference chamber 4 containing a reference volume 3, a radiation source 5 suitable for emission of electromagnetic radiation in the infrared region of the spectrum, and a detector 6 and an evaluation unit 8 connected via a line 7.

The radiation source 5 emits a broadband spectrum of infrared radiation which is collimated by a mirror 9 and afterwards is projected onto a semi-transparent mirror 10. The beam is split by this mirror into a component passing through the mirror which is transmitted to the reference chamber 4 as a reference beam 11, and a reflected component which is transmitted to the test chamber 2 as a test beam 13 after having been deflected once again at a mirror 12.

Both the reference beam 11 and the test beam 13 enter their respective chamber 4 or 2 through windows 14 and leave it through windows 15 after having traversed the chamber, following which they are fed to a common detector 6 via focusing mirrors 16, 17.

In the radiation path of the reference beam 11 and the test beam 13 a selector unit 18 is located between the focusing mirrors 16 and 17, respectively, and the detector 6, which unit in this variant (cf. also FIG. 2) is essentially configured as a rotating disk 19 driven by a mechanism (not shown). This disk 19 has openings 20, 21 containing two different frequency filters for the transmission of radiation of two different, defined frequency bands. These frequency bands may be selected such that the filter located in opening 20 will only transmit a narrow band of wavelengths around 3.95 $\mu$m, and that in opening 21 will only transmit a narrow band of wavelengths around 3.45 $\mu$m, which is of advantage, e.g., if the masses of exhaust gas particles are to be determined.

On the circumference of the disk 19 notches 22 are provided corresponding to the openings 20, 21 and cooperating with a non-contact proximity switch or light barrier 23. Via a line 24 switch 23 is connected to the evaluation unit 8 which in ordinary operating conditions is influenced by the marking signals derived from the notches and arriving via line 24 in such a way that the signals from the detector 6 arriving via line 7 are read and accepted only if the notches 22 indicate maximum congruence between beam 11 or 13 and one of the openings 20/21, and thus maximum intensity of the passed beams.

Detector 6 is a "fast" detector whose time constant is smaller by at least one order of magnitude than the period with which the selector unit 18 alternates between test beam 13 and reference beam 11; in this way the momentary value of the detector signal is sampled at least twice during each period, i.e., at least once for determining the intensity of the test beam and once for that of the reference beam. The sampling time which may be determined by the width of the notches 22, for example, is short relative to the period mentioned above.

For measurement of rapid dynamic processes causing rapid variations of the masses of the absorbing sample components to be determined in test volume 1, the disk 19 of the selector unit 18 should be driven at a speed permitting the desired time resolution, with one of the two beams 11, 13 arriving at the detector 6 after having passed the filters placed in the openings 20 and 21 one after the other, and the other beam following suit during each revolution. In principle, a single measurement of test beam and reference beam at one defined frequency during each period would be sufficient for performance of the measurements. Even if measurements are taken at several frequencies it will not be necessary to determine the intensity of both the test beam and the reference beam at all these frequencies; measuring the test beam 13 at all frequencies and the reference beam 11 at one of these defined frequencies would be sufficient. In the set-up presented here this would be possible, for instance, by providing the disk 19 with only one notch 22 cooperating with the switch 23 for the passage of the reference beam 11. Deviating from the design of the selector unit 18 shown and discussed before, the unit could be designed such that the sequence in which the detector 6 is exposed to radiation is not determined by the beams 11/13 but by the individual frequency bands to be measured; this would only result in the evaluation unit 8 attributing the measurement signals of the detector 6 to the beams in a different way.

From the difference in intensity between the test beam 13 and the reference beam 11 which is determined at the detector 6, the masses of the absorbing sample components to be measured are determined in the evaluation unit 8; the obtained values may be displayed optically or recorded on a data carrier in a suitable manner.

Figure 3:
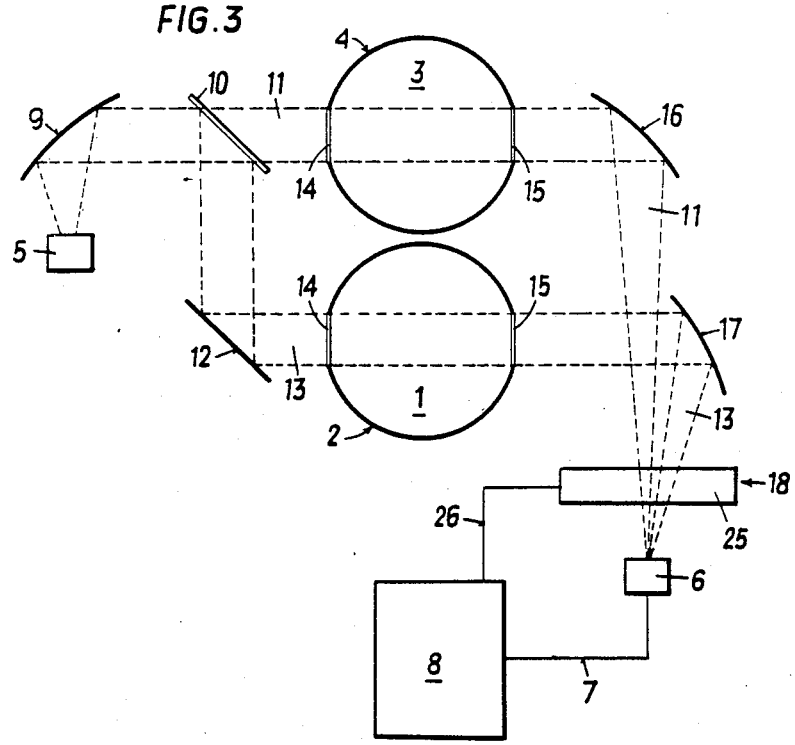

The assembly in FIG. 3 differs from that in FIG. 1 only with regard to the selector unit 18 which is provided here with a frequency-selective element 25 that may be tuned optoeletronically and is connected to the evaluation unit 8 via a line 26 and cooperating with this unit such that the signal of the detector 6 is accepted by the evaluation unit 8 only at those points in time at which the optoelectronic unit 25 is selecting one of the defined frequency bands from the test beam 13 or the reference beam 11.

As regards the other characteristics and advantages of the set-up presented in FIG. 3, please refer to the description of FIG. 1; identical parts are given identical reference numbers.

Figure 2:
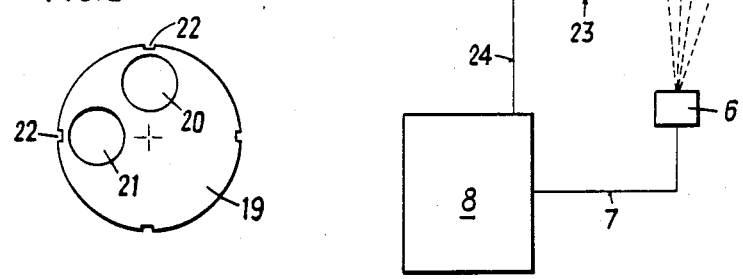
FIG. 2 shows detail II taken from FIG. 1, FIGS. 3, 4 present further embodiments of the invention, the view corresponding to that in FIG. 1.
Figure 4:
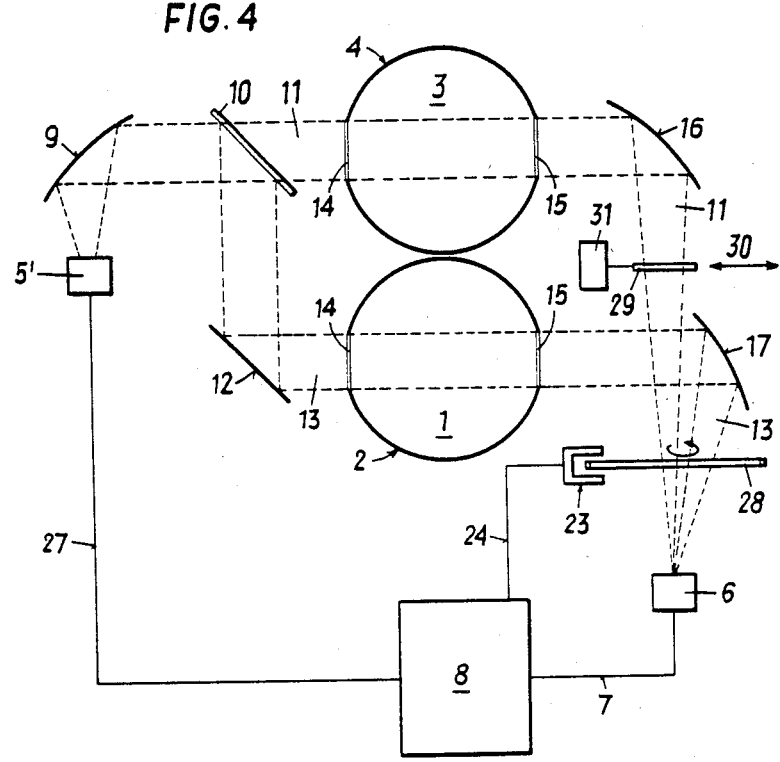

The assembly according to FIG. 4 differs from those in FIGS. 1 to 3 mainly by the use of an infrared source 5' as a radiation source which is connected to the evaluation unit 8 via a line 27 and can be tuned periodically to the desired frequency bands. The selector unit 18 of the variants shown in FIGS. 1 to 3 is thus eliminated;

the only element required here is a chopper disk 28 which is introduced into the radiation path of the reference beam 11 or the test beam 13 in front of the detector 6, alternately passing the two beams 11, 13 to the detector 6. In this variant again a proximity switch 23 or light barrier is used which is connected to the evaluation unit 8 via a line 24 and permits the radiation intensity measured at the detector 6 to be attributed either to the test beam or to the reference beam.

For the remaining properties and benefits please refer to the above descriptions; identical parts again have identical reference numbers.

It should be pointed out moreover that, as is shown in FIG. 4, an absorber 29 of defined absorption may be introduced into the radiation path of the reference beam 11 with a period which is an integral multiple of the period of alternation between test and reference beam. The movement along arrow 30 is performed via an actuating element 31 which is connected to, or influenced by, the evaluation unit 8 in a manner not shown. This will permit continual calibration of the assembly which may compensate influences of fluctuations in the intensity of the radiation source. Deviating from the arrangement shown here, the absorber 29 could also be positioned in the radiation path of the test beam 13.

Figure 5:
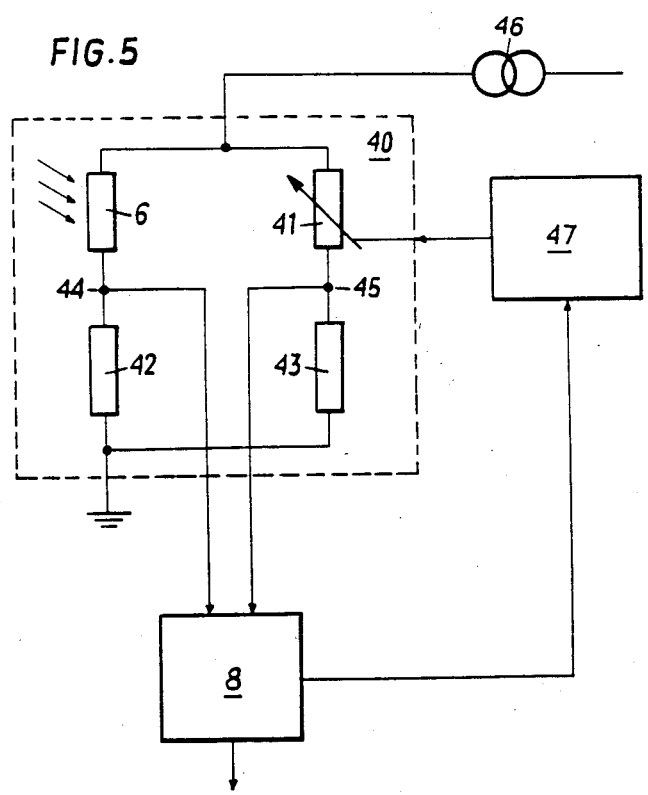
FIG. 5 presents a schematical view of a favorable design of the detector and evaluation unit.

FIG. 5 is a diagram of a favorable design of the detector/evaluation unit. The detector 6 is one out of four resistors in a bridge circuit 40. The resistance value of one of the other resistors 41,42,43 (in FIG. 5, 41 has been chosen) is adjustable, whereas the other two (42,43) have a suitable constant value. The bridge circuit 40 is fed from a constant current source 46. The voltage between two points 44,45 of the bridge is fed to the evaluation unit 8 as a measurement signal. Any change in the conductivity of the photoresistor constituting the detector 6 relative to a reference situation may be detected with a high degree of sensitivity if the variable resistor 41 is set such that the measurement signal in the reference situation is zero.

Small absorptions can be determined particularly well if the maximum exposure of the detector (without absorption) is defined as the reference situation. In this case the degree of absorption is directly correlated with the voltage between points 44 and 45.

Adjustment of the variable resistor 41 may be performed either manually or, as indicated in FIG. 5, by means of electronic or electromechanical control elements 47 which in turn are controlled by the evaluation unit 8.

We claim:

1. A method of determining masses of absorbing components of a sample in a test volume, said method including the steps of (1) providing a test volume which contains the sample with absorbing components, (2) providing a reference volume, (3) deriving at least two frequency bands from one source of electromagnetic radiation, (4) providing a detector which has a certain response time constant, (5) passing separate beams of said electromagnetic radiation through both said test volume and said reference volume, (6) cyclically allowing said separate beams of electromagnetic radiation to alternatively pass to said detector, said cycles being at least one order of magnitude longer than said certain response time constant of said detector, said detector, during each said cycle, detecting the intensity of each frequency band of the beam which has passed through said test volume and at least one frequency band of the beam which has passed through said reference volume, and (7) determining the masses of absorbing components of said sample based on the differences in radiation intensity detected by said detector.

2. A method according to claim 1, including the steps of providing an evaluation unit which is electrically connected to said detector, and causing said detector to emit intensity value signals to said evaluation unit when neither of said separate beams of electromagnetic radiation are passed thereto.

3. A method according to claim 1, wherein said separate beams of electromagnetic radiation provide separate radiation paths, and including the step of cyclically passing an absorber having defined absorption characteristics into said radiation paths, the duration of said cycles of absorber movement into said radiation paths being equal to multiples of the duration of said cycles of separate beam passage to said detector.

4. A method according to claim 1, wherein one of the frequency bands derived in step (3) is centered at 3.95 $\mu$m, thus enabling the measurement of the mass of graphitic aerosol particles in an exhaust gas.

5. An apparatus for determining masses of absorbing components of a sample, said apparatus comprising first chamber means forming a test volume, second means forming a reference volume, a detector, an evaluation unit electrically connected to said detector, radiation means for emitting at least one test beam of broadband infrared radiation which travels through said first chamber means and along a first lightpath towards said detector, as well as one reference beam of broadband infrared radiation which travels through said second chamber means and along a second lightpath towards said detector, and a selector unit located in said first and second lightpaths between said first and second chamber means and said detector for alternatively allowing said test beam and said reference beam to pass therethrough to strike said detector, said selector unit including a mechanical gear system which includes selector elements and frequency filters which allow defined frequency bands of light to pass therethrough.

6. An apparatus for determining masses of absorbing components of a sample, said apparatus comprising first chamber means forming a test volume, second means forming a reference volume, a detector, an evaluation unit electrically connected to said detector, radiation means for emitting at least one test beam of broadband infrared radiation which travels through said first chamber means and along a first lightpath towards said detector, as well as one reference beam of broadband infrared radiation which travels through said second chamber means and along a second lightpath towards said detector, and a selector unit located in said first and second lightpaths between said first and second chamber means and said detector for alternatively allowing said test beam and said reference beam to pass therethrough to strike said detector, said selector unit including at least one frequency-selective unit which can be optoelectronically tuned.

7. An apparatus for determining masses of absorbing components of a sample, said apparatus comprising first chamber means forming a test volume, second means forming a reference volume, a detector, an evaluation unit electrically connected to said detector, radiation means for emitting at least one test beam of broadband infrared radiation which travels through said first chamber means and along a first lightpath towards said detector, as well as one reference beam of broadband infrared radiation which travels through said second chamber means and along a second lightpath towards said detector, and a selector unit located in said first and second lightpaths between said first and second chamber means and said detector for alternatively allowing said test beam and said reference beam to pass therethrough to strike said detector, said detector comprising a resistor in a bridge circuit in said evaluation unit, said bridge circuit including another resistor and two connector points, said another resistor being capable of adjusting the output voltage between said two connector points.

* * * * *